US009894438B2

(12) United States Patent
Kumar et al.

(10) Patent No.: US 9,894,438 B2
(45) Date of Patent: Feb. 13, 2018

(54) ACOUSTIC PROCESSOR HAVING LOW LATENCY

(71) Applicant: Avnera Corporation, Beaverton, OR (US)

(72) Inventors: Amit Kumar, Portland, OR (US); Thomas Irrgang, Portland, OR (US); Xudong Zhao, Portland, OR (US)

(73) Assignee: AVNERA CORPORATION, Beaverton, OR (US)

( * ) Notice: Subject to any disclaimer, the term of this patent is extended or adjusted under 35 U.S.C. 154(b) by 0 days.

(21) Appl. No.: 15/294,556

(22) Filed: Oct. 14, 2016

(65) Prior Publication Data

US 2017/0034619 A1 Feb. 2, 2017

Related U.S. Application Data

(63) Continuation of application No. PCT/US2015/053187, filed on Sep. 30, 2015.

(60) Provisional application No. 62/057,481, filed on Sep. 30, 2014.

(51) Int. Cl.
*A61F 11/06* (2006.01)
*H04R 3/00* (2006.01)
*G10K 11/178* (2006.01)

(52) U.S. Cl.
CPC ........... *H04R 3/005* (2013.01); *G10K 11/178* (2013.01); *G10K 2210/3028* (2013.01); *G10K 2210/3051* (2013.01); *G10K 2210/3056* (2013.01)

(58) Field of Classification Search
None
See application file for complete search history.

(56) References Cited

U.S. PATENT DOCUMENTS 8,090,114 B2 1/2012 Burge et al.
8,848,935 B1 9/2014 Massie et al.
2009/0034748 A1 * 2/2009 Sibbald ................ G10K 11/178 381/71.6
2010/0272275 A1 10/2010 Carreras et al.
2010/0310086 A1 12/2010 Magrath et al.
2011/0001646 A1 1/2011 Koch
2011/0007907 A1 1/2011 Park et al.
(Continued)

FOREIGN PATENT DOCUMENTS

GB 2455828 A 6/2009
WO 2012166273 A2 12/2012

OTHER PUBLICATIONS

International Search Report and Written Opinion for International Application No. PCT/US2015/053187, dated Jan. 25, 2016, 10 pages.

(Continued)

*Primary Examiner* — Joseph Saunders, Jr.
*Assistant Examiner* — James Mooney
(74) *Attorney, Agent, or Firm* — Marger Johnson

(57) ABSTRACT

An audio system having low latency includes a digital audio processor as well as sensor inputs coupled to the processor. The sensor inputs may be microphone inputs. The audio processor operates at the same frequency as the sensor inputs, which is typically much higher than an audio signal provided to the audio processor. In some aspects the audio processor operates as a noise cancellation processor and does not include an audio input.

29 Claims, 5 Drawing Sheets

(56) References Cited

U.S. PATENT DOCUMENTS

| | | | | |
|---|---|---|---|---|
| 2012/0308025 | A1* | 12/2012 | Hendrix ............ | G10K 11/1784 381/71.11 |
| 2014/0112491 | A1 | 4/2014 | Murthy et al. | |
| 2014/0270223 | A1 | 9/2014 | Li et al. | |

OTHER PUBLICATIONS

Notice of Allowance issued in U.S. Appl. No. 14/553,644, dated Jul. 19, 2016, 9 pages.

* cited by examiner

ACOUSTIC PROCESSOR HAVING LOW LATENCY

CROSS REFERENCE TO RELATED APPLICATIONS

This application is a continuation of International Application PCT/US15/53187, entitled ACOUSTIC PROCESSOR HAVING LOW LATENCY, filed Sep. 30, 2015, which claims the benefit of U.S. Provisional Patent Application 62/057,481, entitled ACOUSTIC PROCESSOR HAVING LOW LATENCY, filed Sep. 30, 2014, the contents of which are incorporated herein by reference.

FIELD OF THE INVENTION

This disclosure is directed to acoustic processing, and, more specifically, to a reconfigurable acoustic processor that is capable of running in real-time or near real-time.

BACKGROUND

In general, noise that is present in a listening environment nearly always compromises the experience of listening to audio through headphones. For instance, in an airplane cabin, noise from the airplane produces unwanted acoustic waves, i.e., noise, that travel to the listener's ears, in addition to the audio program. Other examples include computer and air-conditioning noise of an office or house, vehicle and passenger noise in public or private transportation, or other noisy environments.

In an effort to reduce the amount of noise received by the listener, two major styles of noise reduction have been developed, passive noise reduction and active noise cancellation. Passive noise reduction refers to a reduction in noise caused by placing a physical barrier, which are commonly headphones or earplugs, between the ear cavity and the noisy outside environment. The amount of noise reduced depends on the quality of the barrier. In general, noise-reduction headphones having more mass provide higher passive noise reduction. Large, heavy headphones may be uncomfortable to wear for extended periods, however. For a given headphone, passive noise reduction works better to reduce the higher frequency noise, while low frequencies may still pass through a passive noise reduction system.

Active noise reduction systems, also called active noise cancellation (ANC), refers to the reduction of noise achieved by playing an anti-noise signal through headphone speakers. The anti-noise signal is generated as an approximation of the negative of the noise signal that would be in the ear cavity in absence of ANC. The noise signal is then neutralized when combined with the anti-noise signal.

In a general noise cancellation process, one or more sensors (e.g. microphones) monitor ambient noise or noise in the earcups of headphones in real-time, then the system generates the anti-noise signal from the ambient or residual noise. The anti-noise signal may be generated differently depending on factors such as physical shape and size of the ANC system, (e.g., headphones, etc.), frequency response of the sensor and a transducer, e.g. speaker, latency of the transducer at various frequencies, sensitivity of the sensor, and placement of the transducers and sensors, for example. The variations in the above factors between different sensors and transducers (e.g., headphones) and even between the two ear cups of the same headphone system mean that optimal filter design for generating anti-noise also vary.

Latency in processing an anti-noise signal prevents Active Noise Cancellation systems from operating efficiently. For instance, digitizing the sensor signals and processing the signal at rates common in audio processing, such as 44.1 KHz or 48 KHz introduces large latency. Because performance of an acoustic processor, such as an ANC, depends on the ability to detect noise and produce the anti-noise signal soon enough in time to cancel the noise, a large latency is detrimental to acoustic noise cancellation processing.

Embodiments of the invention address this and other limitations of the prior art.

DETAILED DESCRIPTION

Embodiments of the invention are directed to a digital acoustic processor, such as a Reconfigurable Acoustic Processor (RAP) for use in audio systems that use digitized sensor inputs.

Figure 1:
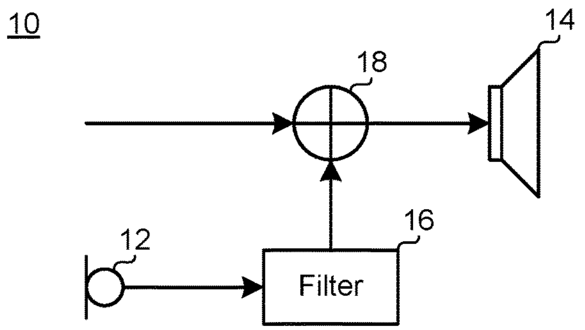
FIG. 1 is a circuit diagram illustrating conventional topology of feed-forward Active Noise Cancellation.

There are three major types of Active Noise Cancellation (ANC), which are distinguished based on sensor, or microphone placement within the system. In feed-forward ANC, the sensor senses ambient noise but does not appreciably sense the signal produced by a transducer, such as a speaker. Such a system is illustrated in FIG. 1. With reference to FIG. 1, a feed-forward ANC system 10 includes a sensor 12 that senses ambient noise, but does not monitor the signal directly from a transducer 14. The output from the sensor 12 is filtered in a feed-forward filter 16 and the filter output coupled to a feed-forward mixer 18, where the filtered signal is mixed with an input audio signal. The filtered signal from the filter 16 is an anti-noise signal produced from the output of the sensor 12. When the anti-noise signal is mixed with the desired signal in the mixer 18, the output of the transducer 14, which is a combination of an input signal mixed with the filtered, anti-noise signal, has less noise than if there were no anti-noise signal generated.

Figure 2:
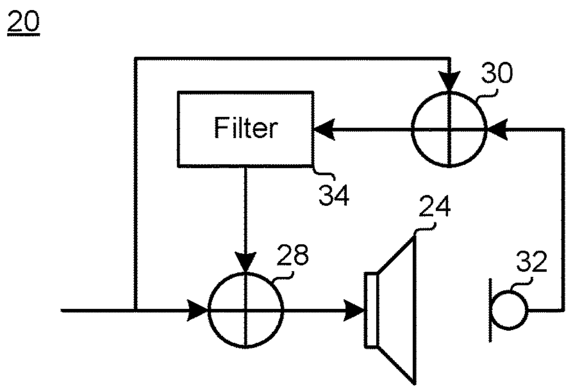
FIG. 2 is a circuit diagram illustrating conventional topology of feed-back Active Noise Cancellation.

In feedback ANC, the sensor is placed in a position to sense the total audio signal present in the ear cavity. In other words, the sensor senses the sum of both the ambient noise as well as the audio played back by the transducer. Such a system is illustrated in FIG. 2. With reference to FIG. 2, in a feedback ANC system 20, a sensor 32 directly monitors output from the transducer 24. The output from the sensor 32 is mixed with the audio input signal in a feedback mixer 30, and then the combined signal sent to a feedback filter 34 where the combined signal is filtered to produce an anti-noise signal. This anti-noise signal from the filter 34 is mixed with the original audio signal in a mixer 28, the combined output of which is then fed to the transducer 24. The feedback ANC system 20 also reduces the noise heard by the listener of the speaker 24.

Figure 3:
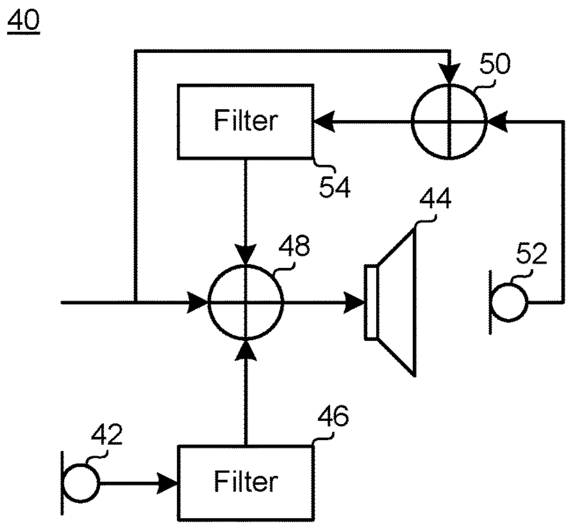
FIG. 3 is a circuit diagram illustrating conventional topology of a combined feed-forward and feed-back Active Noise Cancellation.

A combined feed-forward and feedback ANC system uses two or more sensors, the first position for sensors being in the feed-forward path as illustrated in FIG. 1, and the second position of sensors being in the feedback path as illustrated in FIG. 2. A combined feed-forward and feedback ANC system 40 is illustrated in FIG. 3, and includes sensor positions 42, 52, and one or multiple transducers at the position illustrated in FIG. 44. A signal sensed from the feedback sensor(s) at position 52 is mixed in a feedback mixer 50 and the combined signal filtered by a feedback filter 54. Similarly, a signal sensed from the feed-forward sensors(s) at position 42 is filtered in a feed-forward filter 46 and the filtered signal combined with the incoming audio signal in a feed-forward mixer 48. The output of the transducer(s) at position 44 has reduced noise by the filtering and mixing operations.

Whereas existing systems used fixed topologies and filters, embodiments of the invention use a selectable system to cover many different applications, as described in detail below.

Typical audio processing rates are 44.1 KHz or 48 KHz, which is based on the frequency range of typical human hearing. At these sample rates, the sampling time period is around 20 µs. The digitizing and the filtering in ANC systems invariably take multiple samples. At these rates, the resulting delay is in the order of hundreds of microseconds. Because any delay in processing degrades generation of the anti-noise signal, this significantly lowers ANC performance. This usually manifests itself as limiting the maximum noise frequency that may be cancelled.

Figure 4:
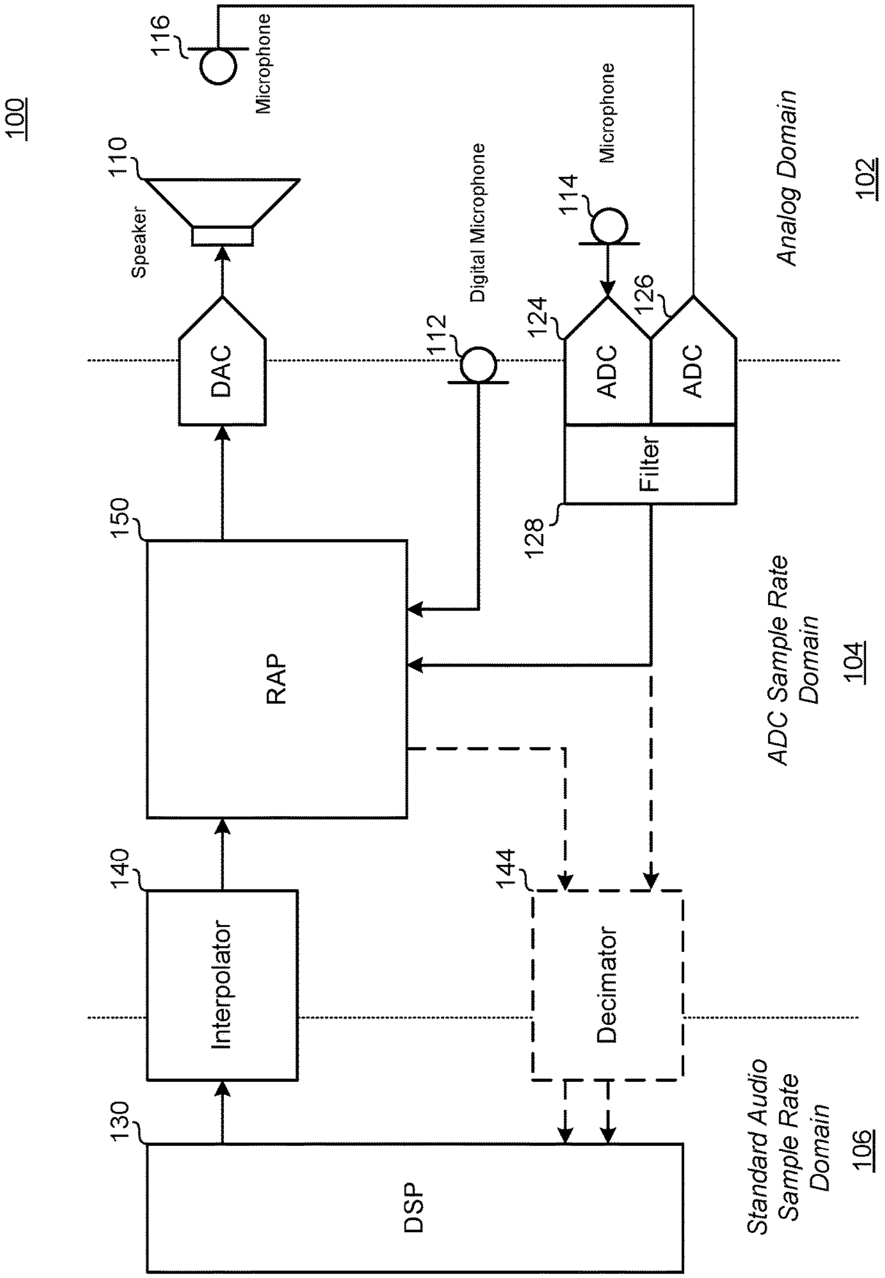
FIG. 4 is a block diagram of an audio system including a reconfigurable acoustic processor according to embodiments of the invention.

FIG. 4 is a block diagram of an audio system 100 including a low-latency or ultra-low latency acoustic processor. In some embodiments the acoustic processor may be reconfigurable, and is referred to as a Reconfigurable Audio Processor (RAP) 150. The audio system in FIG. 4 is divided into three general portions—an analog portion 102, a digital portion 104 running at a rate of an Analog to Digital Converter (ADC), and a digital portion 106 running at a standard audio sample rate, such as 44.1 or 48 KHz. These portions may also be referred to as domains.

The analog portion 102 does not require a clock, and typically signals in this portion are generally continuous, analog, signals. For example a transducer or speaker 110 may produce an analog audio signal such as from headphones or other speakers. A sensor, such as a digital microphone 112 automatically generates a digital output from an analog input signal, while a standard analog sensor, such as microphone 114, may be combined with an ADC 124 to generate a digital signal from the analog sensor 114. A sensor 116, such as a microphone, may be placed in the feedback position, and coupled to an ADC 126. The ADCs 124, 126 may use sigma-delta processing, for example. In other embodiments the ADCs 124, 126 may be of Pulse Code Modulation (PCM) or Successive Approximation Register (SAR) type. A single sensor 112, 114, 116 may be used for multiple purposes, such as sampling ambient noise while also serving as an input microphone for a telephone, for example. One or more filters 128 may be present to filter outputs from the ADCs 124, 126, but are not required in all embodiments.

A Digital Signal Processor (DSP) 130 or other audio source operates in the digital portion 106 and at a frequency of a standard audio sample rate. Typically the operating frequency of the digital portion 106 of the audio system 100 may be 44.1 or 48 KHz.

The operating frequency of the digital portion 104, conversely, may operate from a low of approximately 50 KHz to a rate of approximately 100 MHz, and preferably within a range such as 2-100 MHz. In some embodiments the digital portion 104 may operate at 50 KHz, 96 KHz, within a range of hundreds of KHz, at frequencies in the low MHz range, such as 1-6, in the 10 s of MHz range, such as 10-20 MHz, up to approximately 100 MHz. In embodiments of the invention, each of the components of the particular domain operates at the frequency of the domain. For example, with reference to FIG. 4, the ADCs 124, 126 operate at the same frequency as the audio processor or RAP 150. This is quite different than previous systems that typically use decimation filters to downsample sensor signals before processing in an audio processor.

An interpolator 140 converts audio signals from the DSP 130, for example operating at 48 KHz, to audio signals operating at 3 MHz or 6 MHz as an input signal to the RAP 150. In reverse, a decimator 144, which need not be present in all audio systems 100, converts signals from the RAP 150 at, for instance 3 or 6 MHz, to the operating frequency of the digital portion 106. The resulting latency of the RAP 150 is extremely low, for example less than 2.5 µs, and preferably less than 0.5 µs, because the RAP 150 processes signals at the same rate as they are generated by the sensors, or microphones 112, 114, 116, whether or not the sensors are digital microphones or whether the sensor signals are converted by the ADCs 124, 126 to digital signals.

As described in more detail below, the RAP 150 controls acoustic signals, for example emitted from the transducer 110, in real time. As described above, the RAP 150 is structured to operate on raw sensor samples from the microphones 112, 114, and/or 116 without any intermediate processing, like a decimation filter or other sample rate converters. This allows responding to microphone signals with zero or near zero computational delay in the RAP 150, which enables implementation of real-time audio processing algorithms. The effect of using real-time sensor sampling is that delay from the decimation filter of previous systems is eliminated, which in turn dramatically increases the responsiveness of the control loop.

The sample rate of the digital portion 104 may be varied according to a sample rate of the digital sensor 112, or the ADC 124 coupled to the analog sensor 114. There is a linear tradeoff between the sample rate and the amount of processing that may be processed per sample.

Figure 5:
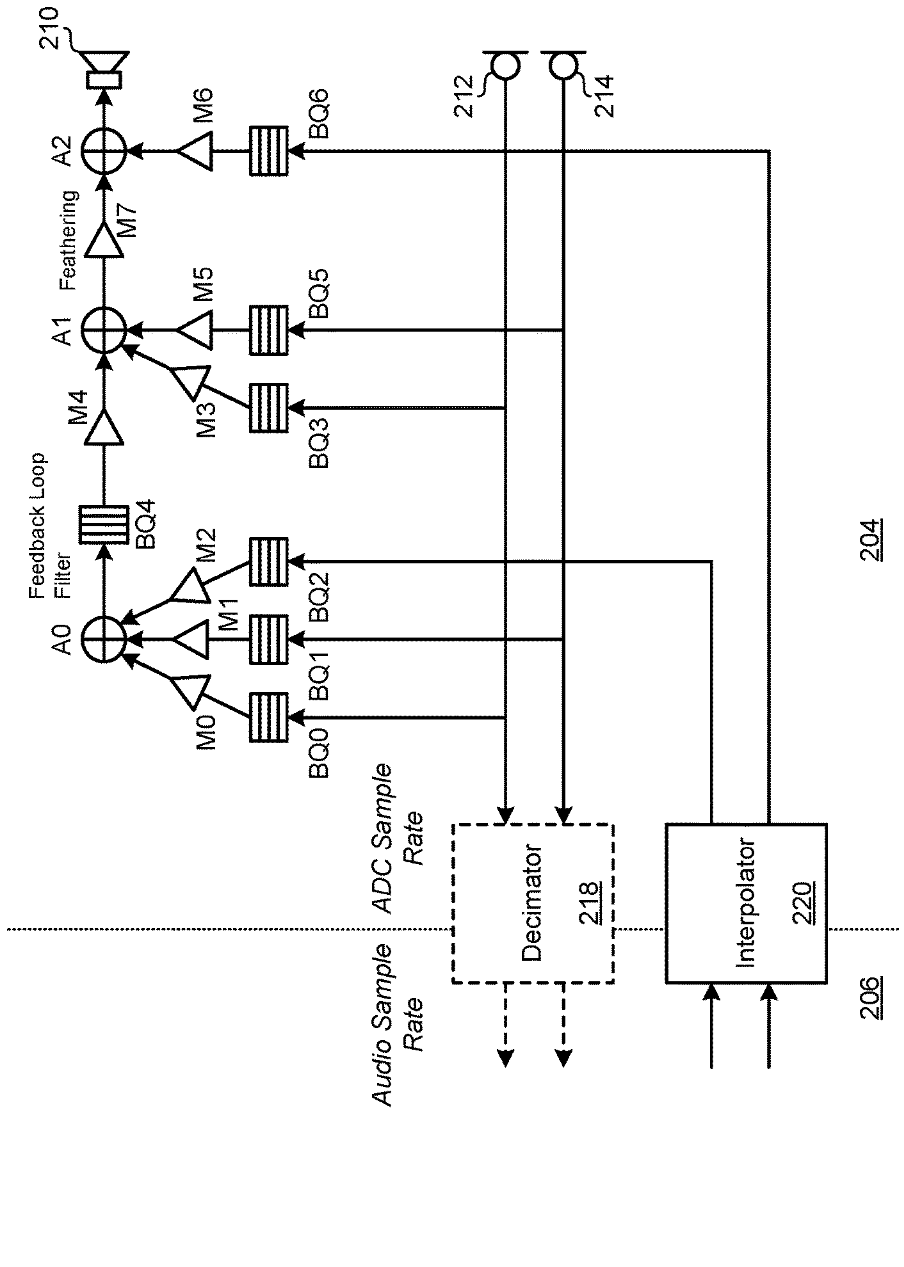
FIG. 5 is a functional block diagram of an example reconfigurable acoustic processor of FIG. 4.

FIG. 5 is a functional block diagram of an example reconfigurable acoustic processor (RAP) 250, which may be an embodiment of the RAP 150 of FIG. 4. The RAP 250 of FIG. 5 includes six chains of bi-quadratic, or bi-quad filters, BQ0-BQ6, the functions of which are described below. Bi-quad filters are well known in electrical processing, especially audio processing. Bi-quad filters typically include 2 zeros and 2 poles. The bi-quad chains BQ0-BQ6 each include a cascade of bi-quad filters. In some embodiments the chains BQ0-BQ6 may include 4, 6, 8, 12, or 16 cascaded bi-quad filters, with 8 being preferred. The bi-quad filter chains BQ0-BQ6 are programmable, so that their filtering values may be changed according to a desired implementation. They may also be set to a pass-through, or unity, setting, which means they do not appreciably affect the signal passing through them.

Connected to each bi-quad filter chain BQ0-BQ6 are gain units, M0-M6, respectively, with an additional gain unit M7, the purpose of which is described below. The gain units M0-M7 are programmable, in that the amount of gain produced between their inputs and outputs is controllable. Output of particular bi-quad filter chains BQ0-BQ6 may be controlled by its coupled gain unit M0-M6. Setting the gain of any of the gain units M0-M6 to zero effectively turns off that particular circuit branch. It is not strictly necessary to maintain a one-to-one relationship between bi-quad filter chains and gain units, but maintaining that relationship provides flexibility for setting up the RAP. The RAP 250 of FIG. 5 shows a single audio channel. For two or more channels, such as for stereo processing, additional hardware would be used.

By programming particular filter coefficients in the bi-quad filter chains BQ0-BQ6 and particular gain values in the gain units M0-M6, different audio applications may be performed in the RAP 250, such as audio noise cancellation, as described below.

Also coupled to the RAP 250 may include inputs from digital sensors, 212, 214, which may be microphones, a decimator 218, and an interpolator 220. Either or both of the sensor inputs 212, 214 may be created by having an analog microphone coupled to an ADC. The decimator 218 and interpolator 220 operate as described with reference to FIG. 4.

In operation, the RAP 250 accepts input from the sensor 212 at bi-quad filter chains BQ0 and BQ3, and accepts input from the sensor 214 at bi-quad filter chains BQ1 and BQ5. An audio signal is accepted at the bi-quad filter chains BQ2 and BQ6. In some embodiments, an audio signal is not strictly necessary. For example, in noise cancellation headphones for hunters or industry, no audio signal may be present.

The gain unit M7 may be used as a controllable gain for the processed audio signal before its final combination in a combiner A2 with the unprocessed audio signal from the interpolator 220. The gain unit M7 may be controlled to increase its gain gradually, so that noise cancelation or other processing may be added to the unprocessed audio signal gradually, to eliminate pops or other fast changes in the output audio signal, which may be uncomfortable for a listener.

Adders or combiners A0, A1, and A2 combine intermediate signal outputs from the bi-quad filter chains, as illustrated in FIG. 5.

In one embodiment, the RAP 350 operates at 49.152 MHz, which is a standard rate for audio processing. The input sample rate is typically 3.072 Msps, and the filter portion may also operate at the same rate.

A straightforward example of operation of the RAP 250 is a simple audio processor, without using input from either of the sensors 212, 214. In such an example, the gain unit M7 is set to 0, i.e., turned off, while the audio signal from the interpolator is filtered by the bi-quad filter chain BQ6. Controlling the gain unit M6 controls an output signal level of the filtered audio signal, which is sent to the transducer 210, which may be a speaker, or other transducer output.

Figure 6:
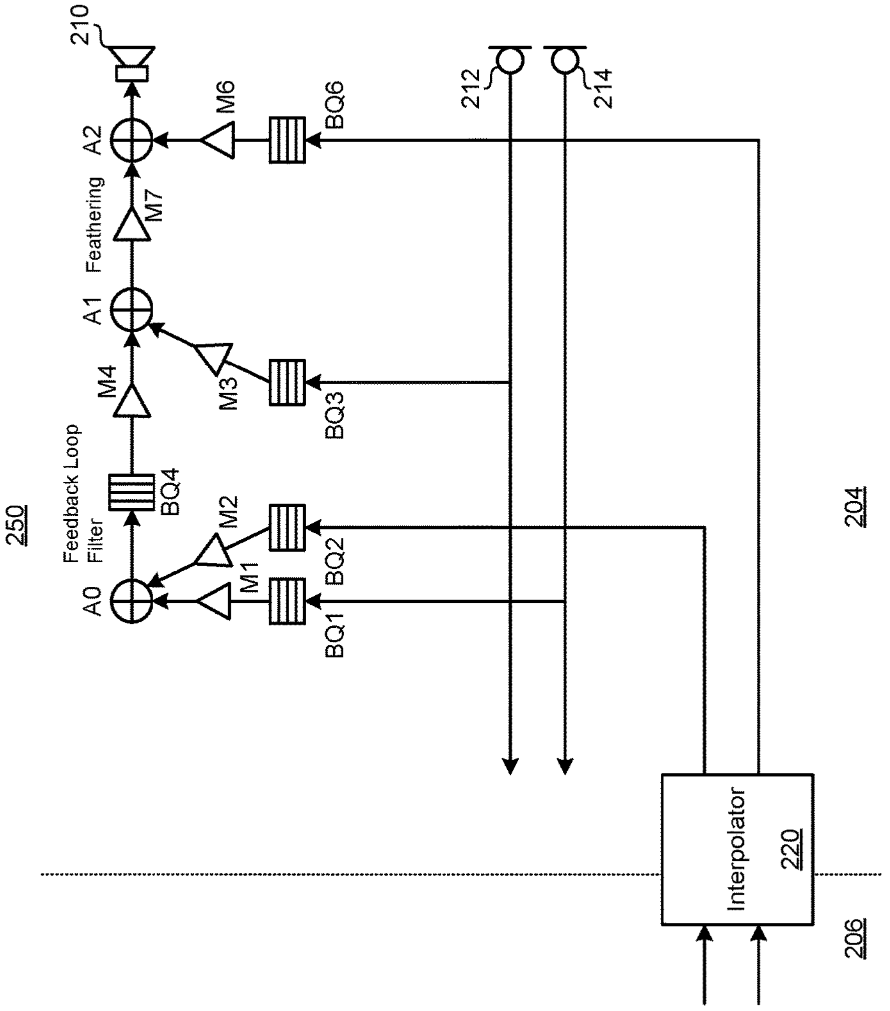
FIG. 6 is a block diagram that illustrates the reconfigurable acoustic processor of FIG. 4 configured to implement combined feed-forward and feed-back Active Noise Cancellation operations.

In a more complex example, the RAP 250 may be configured as a feed-forward/feedback ANC, having the same functionality as the feed-forward and feed-back ANC circuit illustrated in FIG. 3. FIG. 6 illustrates how the RAP 250 is set for such a configuration. In this configuration, the gain units M0 and M5 are set to 0, which is illustrated in FIG. 6 as having an "x", which indicates they do not contribute anything to the processing. The gain units M2, M4, M6 and M7 are set to 1. Gain units M1 and M3 are set to −1, which means their outputs are subtracted. Bi-quad filter chains BQ1, BQ2, and BQ6 are set to pass-through settings. With reference to FIGS. 3 and 6, the Bi-quad filter chain BQ3 has the role of the feed-forward filter 46, while Bi-quad filter chain BQ4 has the role of the feedback filter 54.

By configuring the RAP 250, and particularly the gain units M0-M7 and bi-quad filter chains BQ1-BQ6, the RAP may be configured to perform most any type of audio processing. For instance, the RAP 250 may be configured as an ANC processor for active noise cancellation headphones, in either feedback, feed-forward, or combined feed-forward feedback configurations. The RAP 250 may be used for active noise cancellation in phone handsets by using input from the handset microphone and producing audio output for one or more speakers in the handset. The RAP 250 may further enhance an input audio signal while simultaneously performing noise cancellation. The RAP 250 may also be used for ambient sound enhancement by accepting an ambient sound at one of the microphone inputs, modifying it through one or more bi-quad filter chains, setting an appropriate gain level, then outputting the modified ambient signal.

In practice, the RAP 250 of FIG. 6 or RAP 150 of FIG. 5 includes functions, processes, or operations for modifying an audio signal input. In practice these functions may be implemented by specially formed hardware circuits, as programmed functions operating on a general-purpose or special-purpose processor, such as a Digital Signal Processor (DSP), or may be implemented in Field Programmable Gate Arrays (FPGAs) or Programmable Logic Devices (PLDs). Other variations are also possible.

Figure 7:
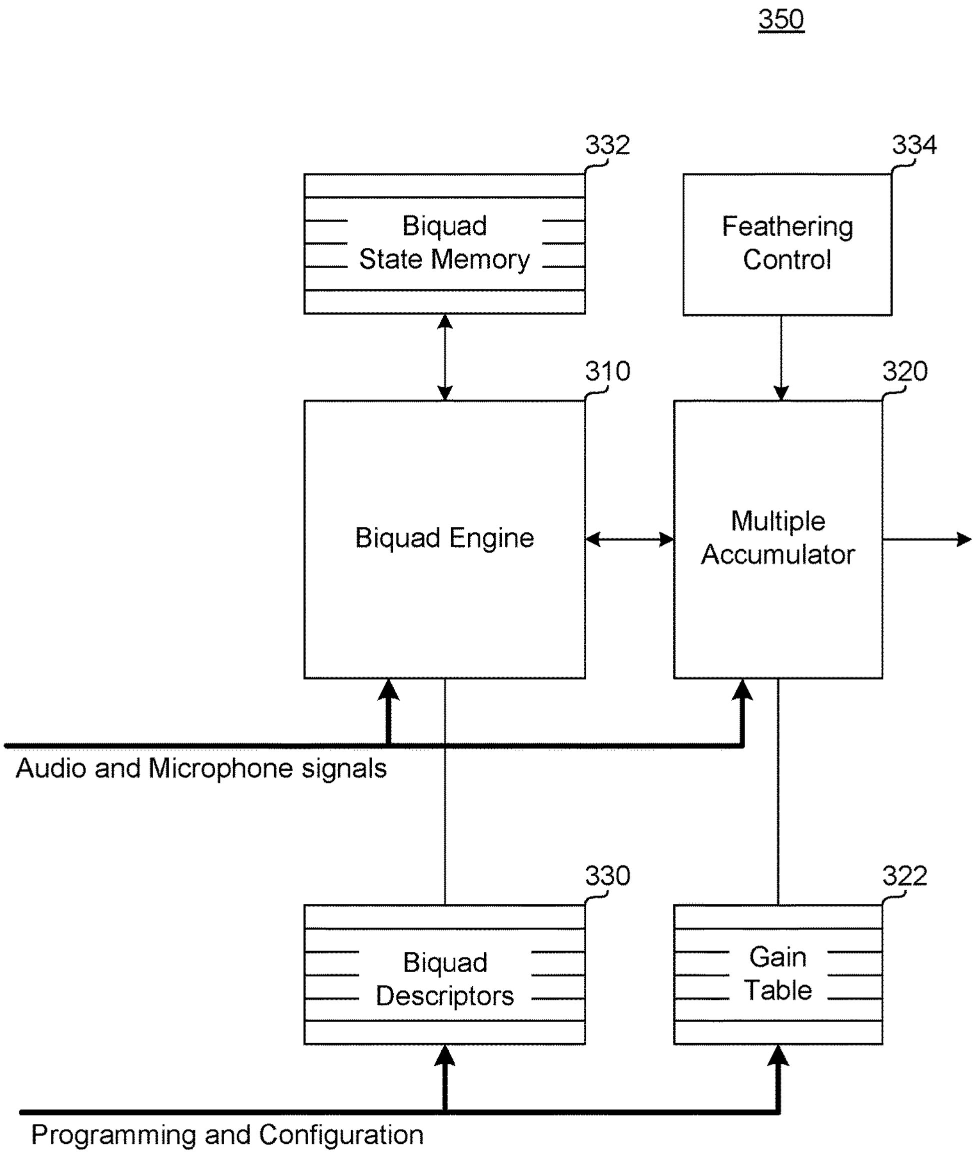
FIG. 7 is a functional block diagram of components of an example reconfigurable acoustic processer of FIG. 4, according to embodiments of the invention.

FIG. 7 is a functional block diagram of components of an example reconfigurable acoustic processor of FIG. 4, according to embodiments of the invention. In FIG. 7, a RAP 350 includes a bi-quad engine 310 and a multiplier accumulator 320. The multiplier accumulator 320 implements all of the multipliers and adders in the functional block diagram of FIGS. 5 and 6. In one embodiment there are seven multiply-add operations per sample. The bi-quad engine 310 includes inputs from one or more sensors, such as microphones, as well as an input of the audio signal to be processed. The biquad engine may also accept input from the multiplier-accumulator output. The inputs from the sensors are clocked at the same rate as the biquad engine. In other words, the sensor inputs may be processed without any decimation or rate reduction. The bi-quad engine 310 may be sized to operate on 16 bi-quad filters. A bi-quad descriptor section 330 contains filter values for implementing the bi-quad filter chains, while bi-quad state memory 332 is memory for storing intermediate values during bi-quad processing. A gain table 322 stores values for the gain units, while feathering control, such as provided by gain unit M7 of FIG. 5, is provided separately by a feathering control 334. The RAP 350 is programmed and configured by writing particular values into the bi-quad descriptors 330 and gain tables 322, as illustrated in FIG. 7.

By using such programmable techniques, filters may be chosen to enhance, rather than reduce certain sounds or noises. For instance, instead of bi-quad chain filter parameters chosen for their ability to reduce sounds sensed by a particular microphone, as described above, parameters may be chosen that enhance particular sounds. For example, a person may be using noise cancellation headphones in a noisy work environment with a variety of rumbling machinery, but still wants to be able to speak to a co-worker without removing the noise reducing headphones. Using the adaptive filter coefficients, when microphones detected noise in the vocal band, different parameters may be automatically loaded to the RAP system that enhanced the voice of the co-worker. Thus the listener would have noise-canceling headphones that adaptively enhanced particular sounds. Sounds such as voices, audio television signals, and traffic, for example, may be enhanced. When such sounds went away, for example the co-worker stopped speaking, the standard filtering coefficients could again be dynamically loaded into the filters of the RAP system.

Embodiments of the invention may be incorporated into integrated circuits such as sound processing circuits, or other audio circuitry. In turn, the integrated circuits may be used in audio devices such as headphones, mobile phones, portable computing devices, sound bars, audio docks, amplifiers, speakers, etc.

Having described and illustrated the principles of the invention with reference to illustrated embodiments, it will be recognized that the illustrated embodiments may be modified in arrangement and detail without departing from such principles, and may be combined in any desired manner. And although the foregoing discussion has focused on particular embodiments, other configurations are contemplated.

In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

Consequently, in view of the wide variety of permutations to the embodiments described herein, this detailed description and accompanying material is intended to be illustrative only, and should not be taken as limiting the scope of the invention.

What is claimed is:

1. An audio system, comprising:

a sensor generating an analog sensor signal;

an Analog to Digital Converter (ADC) coupled to the sensor, the ADC to generate a digital sensor signal from the analog sensor signal at a sample rate that is higher than 50 Kilohertz (KHz);

a digital audio processor performing Active Noise Cancellation (ANC) in a digital domain at the sample rate of the ADC without intermediate sample rate converters, the digital audio processor having a first input for receiving an input audio signal at the sample rate, having a second input for receiving the sensor signal at the sample rate, and having an output, wherein the digital audio processor is structured to employ the sensor signal to perform noise cancelation on the input audio signal to provide a modified signal to the output the digital audio processor including one or more controllable gain stages structured to apply a gain to the sensor signal to process the sensor signal at the sample rate, wherein the one or more controllable gain stages are structured to be programmed during operation of the audio system to controllably adjust the gain of the sensor signal received at the digital audio processor to controllably adjust a level of noise cancelation performed on the input audio signal.

2. The audio system of claim 1, in which the sensor is a microphone, and in which the microphone is part of a system that includes the microphone coupled to the Analog to Digital Converter (ADC), and an output of the ADC is the sensor signal.

3. The audio system of claim 2, in which the ADC is configured to perform Sigma-Delta processing.

4. The audio system of claim 2, in which the ADC is configured to perform Successive Approximation Register (SAR) processing.

5. The audio system of claim 1, in which the output is coupled to a transducer, and in which the transducer is a speaker.

6. The audio system of claim 1, in which the sample rate is a rate of 200 KHz or faster.

7. The audio system of claim 1, in which the sample rate is a rate of 350 KHz or faster.

8. The audio system of claim 1, in which the sample rate is a rate of 750 KHz or faster.

9. The audio system of claim 1, further comprising an interpolator having an input for receiving a digital audio signal at a second rate and converting it to the audio signal having the sample rate.

10. The audio system of claim 9, in which the second rate is lower than the sample rate.

11. The audio system of claim 1, in which the digital audio processor comprises one or more programmable filters electrically coupled to the sensor, wherein the one or more programmable filters are structured to be programmed during operation of the audio system to controllably adjust the sensor signal received at the digital audio processor to adjust the noise cancelation performed on the input audio signal.

12. A reconfigurable noise cancelation system, comprising:

an input for receiving a digital audio signal at an audio sample rate;

an interpolator for changing a sample rate of the digital audio signal from the audio sample rate to an Analog to Digital Converter (ADC) sample rate that is higher than the audio sample rate, the ADC sample rate including a sampling rate in excess of 50 KHz;

at least one sensor producing an analog sensor signal;

an ADC coupled to the sensor, the ADC to generate a digital sensor signal from the analog sensor signal at the ADC sample rate; and a reconfigurable digital audio processor coupled to the interpolator and to the sensor, the reconfigurable digital audio processor performing Active Noise Cancellation (ANC) in a digital domain at the ADC sample rate without intermediate sample rate converters and including:

a plurality of programmable filters structured to be programmed during operation of the reconfigurable noise cancellation system;

a plurality of controllable gain stages, at least some of the plurality of controllable gain stages coupled respectively to at least some of the plurality of programmable filters, the gain stages operating to controllably process the sensor signal at the second rate;

adders structured to combine outputs of one or more of the plurality of controllable gain stages; and an audio output coupled to at least one of the adders for conveying an output audio signal that is modified from the input audio signal.

13. The reconfigurable noise cancelation system of claim 12, further comprising a digital sampling microphone operating at the ADC sample rate.

14. The reconfigurable noise cancelation system of claim 12, in which the at least one sensor is an analog microphone.

15. The reconfigurable noise cancellation system of claim 12, in which the ADC is configured to perform Sigma-Delta processing.

16. The reconfigurable noise cancellation system of claim 12, in which the ADC is configured to perform Successive Approximation Register (SAR) processing.

17. The reconfigurable noise cancelation system of claim 12, in which at least some of the plurality of controllable gain stages are structured to be updated during operation of the reconfigurable noise cancellation system.

18. A method of operating an audio system, comprising:

operating a digital audio processor at an Analog to Digital Converter (ADC) sample rate that is 50 KHz or higher;

receiving, at the digital audio processor, a digital input audio signal having the ADC sample rate, receiving, at the digital audio processor, a digital sensor signal having the ADC sample rate via an ADC without intermediate sample rate converters;

performing Active Noise Cancellation (ANC) on the digital input audio signal in the digital audio processor in a digital domain while running at the ADC sample rate by combining the digital input audio signal with a signal derived from the digital sensor signal to perform noise cancelation on the digital input audio signal, the digital audio processor including gain stages controllably adjusted to process the sensor signal at the first rate;

controllably adjusting a gain of the signal derived from the digital sensor signal to controllably adjust a level of noise cancelation performed on the digital input audio signal during operation of the audio system; and outputting the processed digital input audio signal at an output.

19. The method of operating an audio system of claim 18, in which receiving the digital sensor signal having the ADC sample rate comprises receiving a microphone signal at the ADC sample rate.

20. The method of operating an audio system of claim 19, in which outputting the processed digital input audio signal at an output comprises outputting the digital input audio signal to a transducer.

21. The method of operating an audio system of claim 18, in which the ADC sample rate is a rate of 96 KHz or faster.

22. The method of operating an audio system of claim 18, in which the ADC sample rate is a rate of 1 MHz or faster.

23. The method of operating an audio system of claim 18, in which the ADC sample rate is a rate of 3 MHz or faster.

24. The method of operating an audio system of claim 18, in which the ADC sample rate is a rate of 6 MHz or faster.

25. The method of operating an audio system of claim 18, further comprising:

receiving a digital audio signal at an audio sample rate;

converting the digital audio signal from the audio sample rate to the ADC sample rate; and sending the digital audio signal to the digital audio processor at the ADC sample rate.

26. The method of operating an audio system of claim 25 in which the audio sample rate is 100 KHz or slower.

27. The method of operating an audio system of claim 18, further comprising modifying a programmable filter during operation to controllably adjust the noise cancelation performed on the digital input audio signal during operation of the audio system.

28. A method of operating a reconfigurable noise cancellation processor, comprising:

receiving an audio signal through an audio input at an Analog to Digital Converter (ADC) sample frequency;

receiving one or more sensor signals of a monitored environment at the ADC sample frequency through one or more sensor inputs via an ADC without intermediate sample rate converters, the ADC sample frequency including a sampling rate in excess of 50 KHz;

configuring, prior to receiving the audio signal and sensor signals, a filter parameter section of a plurality of programmable filters in the reconfigurable noise cancellation processor;

configuring, prior to receiving the audio signal and sensor signals, a plurality of controllable gain stages in the reconfigurable noise cancellation processor, at least some of the plurality of controllable gain stages coupled respectively to at least some of the plurality of programmable filters;

controllably adjusting the controllable gain stages to controllably process the audio signal and the sensor signal at the ADC sample frequency;

performing Active Noise Cancellation (ANC) at the ADC sample frequency by mixing one or more outputs of the plurality of controllable gain stages with the audio signal to produce a modified audio signal output; and modifying the filter parameter section of the plurality of programmable filters during operation of the reconfigurable noise cancellation processor.

29. The method of operating a reconfigurable noise cancellation processor according to claim 28, further comprising modifying a gain of at least one of the plurality of controllable gain stages during operation of the reconfigurable noise cancellation processor to control a level of noise cancelation in the modified audio signal output.

* * * * *